(12) United States Patent
Kobayashi et al.

(10) Patent No.: US 7,891,025 B2
(45) Date of Patent: Feb. 22, 2011

(54) PROTECTIVE DEVICE FOR EYES

(75) Inventors: Hirokazu Kobayashi, Osaka (JP);
Kimio Matsumoto, Osaka (JP);
Koichiro Oka, Osaka (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 776 days.

(21) Appl. No.: 11/891,115

(22) Filed: Aug. 9, 2007

(65) Prior Publication Data
US 2008/0055538 A1 Mar. 6, 2008

(30) Foreign Application Priority Data

Aug. 10, 2006 (JP) .............................. 2006-218852
Oct. 27, 2006 (JP) .............................. 2006-292258

(51) Int. Cl.
*A61F 9/02* (2006.01)
(52) U.S. Cl. ............................................. 2/436; 2/440
(58) Field of Classification Search ................... 2/435, 2/436, 440, 442
See application file for complete search history.

(56) References Cited

U.S. PATENT DOCUMENTS 4,290,673 A * 9/1981 Yamamoto ................... 351/62
5,018,223 A * 5/1991 Dawson et al. ................. 2/436
5,689,834 A * 11/1997 Wilson ........................... 2/436
6,009,564 A * 1/2000 Tackles et al. .................. 2/436
6,611,966 B1* 9/2003 Yamamoto et al. ............. 2/436
6,772,448 B1* 8/2004 Hockaday et al. .............. 2/435

FOREIGN PATENT DOCUMENTS

| CN | 1782784 | 6/2006 |
|---|---|---|
| EP | 1661534 | 5/2006 |
| JP | 2002-505157 | 2/2002 |
| WO | WO 2007/085001 | 7/2007 |

* cited by examiner

*Primary Examiner*—Katherine Moran
(74) *Attorney, Agent, or Firm*—DLA Piper LLP (US)

(57) ABSTRACT

A protective device for eyes, for example, goggles of a shield, includes a double lens member, a frame member and a face fixation member. The double lens member includes a front lens, a back lens and a gasket. The front lens and the back lens are made of polycarbonate resins, polyurethane resins, polyester resins or polyamide resins. The front lens and the back lens are disposed in parallel with the gasket therebetween in order to form a space surrounded with the front lens, the back lens and the gasket. This device is excellent in the antifogging property in the double lens.

12 Claims, 5 Drawing Sheets front ⟷ back front ⟵⟶ back

PROTECTIVE DEVICE FOR EYES

INCORPORATION BY REFERENCE

The present invention claims priority under 35 U.S.C. §119 to Japanese Patent Application No. 2006-218852 filed on Aug. 10, 2006 and Japanese Patent Application No. 2006-292258 filed on Oct. 27, 2006. The content of the applications is incorporated herein by reference in its entirety.

BACKGROUND OF THE INVENTION

1. Field of the Invention

This invention relates to a protective device for eyes, particularly goggles or face shielded helmets for sports to be used in skiing, snowboarding, ice skating, cycling, motocross motorcycling etc. as well as industrial goggles or face shields to be used in a building site, civil engineering work and the like.

Especially, the invention relates to goggles, face shielded helmets and face shields excellent in a function of protecting eyes from impact, rain, snow, dust, or the like and hardly fogged in the double lens even in the case of sweating or ambient temperature fluctuation.

2. Description of the Related Art

In sports accompanied with speeds such as skiing, snowboarding, ice skating, cycling and motocross motorcycling, goggles and face shielded helmets for covering both eyes have been widely used for protecting the wearer's eyes from unexpected accident such as a fall and a crash and also for keeping a clear visibility at the time of raining, snowing, or the like.

Further, goggles and face shields have been widely used for protecting the wearer's eyes in so-called dusty work sites of, for example, demolition of buildings, earth and sand collection and stone crushing, tunneling, mining, cement production, and steelmaking.

These goggles and shields are called as a single lens since they typically have a single lens.

For goggles, face shielded helmets and shields, it is indispensable to have a damage-preventing function for protecting eyes from a fall or a crash and a foreign substances-shutting function for protecting eyes from rain, snow, and dust. However, these goggles and shields have been insufficient in anti-fogging function for preventing lens from fogging due to sweating or ambient temperature fluctuation in use.

The foreign substances-shutting function depends on the structure itself of covering both eyes, and therefore this function does not depend on the property of a resin to be used for the lens. On the other hand, the damage-preventing function depends on the property of the base material of the lens, such as bending rigidity and impact-resistant strength. Since polycarbonates are recognized as a material having good stiffness, a strong toughness and difficulty of being bent, polycarbonate lenses have been generally used.

With respect to the antifogging function of goggles and shields, a method for forming an antifogging coating on the inside of the lens, that is the side facing to eyes, has been employed. However, any antifogging agent has a limited capacity in absorbing moisture and once a prescribed amount of moisture is absorbed, droplets are likely to be formed on the antifogging coating, resulting in the lens being fogged.

Moreover, since the goggles and shields forms a kind of sealed space between the skin and the lens facing to the eyes, the moisture such as sweat supplied constantly from the skin tends to filled in that space. Therefore, it is inevitable to cause fogging sooner or later while wearing the goggles or shields, and it is thus difficult to give them a semi-permanent antifogging property.

For such a limited antifogging function, a double lens structure in which two lenses arranged approximately in parallel are fixed by gaskets placed on the circumferential part of the lenses, that is called a double lens, has been proposed.

For the lens facing to the outside, that is a front lens out of two lenses composing the double lens, polycarbonate resins have been commonly used as before in order to obtain the damage-preventing function.

On the other hand, for the lens facing to the eyes, that is a back lens, acyl cellulose resins having a moisture absorbing property have been used. Acyl cellulose, especially, propyl cellulose is preferably used.

In the double lens structure, the space formed by the two lenses and the gasket functions as a temperature buffer zone, so that the cooling inside of the goggle can be moderated even if it is exposed to the cold outside air.

Accordingly, the water vapor enclosed in the space between the lens and the skin is less likely to cause a dew condensation on the back lens, and even if a dew condensation is occurred, since they are absorbed in the propyl cellulose, fogging of the lens facing to the eyes of the double lens is less generated as compared with the goggles with the single lens structure.

However, since the acryl cellulose type resins generally have high moisture permeability, the water vapor enclosed in the space between the lens and the skin through a back lens made of propyl cellulose is easily permeated to the inside space surrounded with the front lens, the back lens and the gasket and this causes a problem that the inside of the front lens, that is the back curve side of the front lens, is fogged when a wearer goes outside like an environment at a temperature of about −5° C. in a skiing area from inside of a warm room.

To deal with this problem, it is proposed to form an antifogging coating on the back curve side of the front lens (Japanese Patent Application National Publication No. 2002-505157)

DISCLOSURE OF THE INVENTION

However, it is not technically easy in production process to form an antifogging coating only on the back curve side of the front lens of an injection molded polycarbonate resin.

For example, if it is carried out by a simple dipping method, the antifogging coating is formed simultaneously on the front curve side besides the back curve side. In such a case, since the antifogging coating generally has low hardness, if the front lens surface is wiped to remove stains, the antifogging coating is scratched and becomes just like frosted glass to give an inferior visibility.

Further, even if the antifogging coating is formed only on the back curve side of the front lens by employing difficult techniques, since the antifogging coating is generally inferior in the strength and adhesion strength to a substrate, the adhesion and sticking between the coating on the back curve side of the front lens and the gasket is soon broken away and therefore it is difficult to make a double lens having high durability.

BRIEF SUMMARY OF THE INVENTION

The present invention is made in order to solve the above noted problems.

Thus, a protective device for eyes of the present invention includes a double lens member, a frame member and a face fixation member. The double lens member includes a front lens, a back lens and a gasket and the front lens and the back lens are made of polycarbonate resins, polyurethane resins, polyester resins or polyamide resins. The front lens and the back lens are disposed in parallel with the gasket therebetween in order to form a space surrounded with the front lens, the back lens and the gasket.

The front lens may have an aspheric shape, a spherical shape or a cylindrical shape, and be made thinner from a center toward a lens rim for a refraction collection.

The back lens may be made from a lens sheet or a molded sheet with a thickness of 0.3 to 3 mm, and have an aspheric shape, a spherical shape and a cylindrical shape approximately same as the front lens.

The front lens may also be made from a lens sheet or a molded sheet with a thickness of 0.3 to 3 mm and the double lens member may have a cylindrical shape.

The back curve side of the back lens may be treated with an antifogging agent.

A resin sheet with antifogging properties having an aspheric shape, a spherical shape or a cylindrical shape approximately same as the back lens may be layered on a back curve side of the back lens.

The gasket may be made of a resin with a thickness of about 0.5 to 7 mm and a width of about 2 to 10 mm. The back curve side of the front lens and the front curve side of the back lens may be fixed via the gasket with a binding agent or an adhesive agent.

At least one pressure adjusting hole nay be provided at the back lens for a pressure adjustment of the space surrounded with the front lens, the back lens and the gasket.

The pressure adjusting hole may be provided at the gasket or an air-permeable gasket may used for a pressure adjustment of the space surrounded with the front lens, the back lens and the gasket.

The pressure adjusting hole and the air-permeable gasket may be covered with a breathable member which is permeable to water vapor but impermeable to water.

DESCRIPTION OF THE PREFERRED EMBODIMENTS

Figure 1:
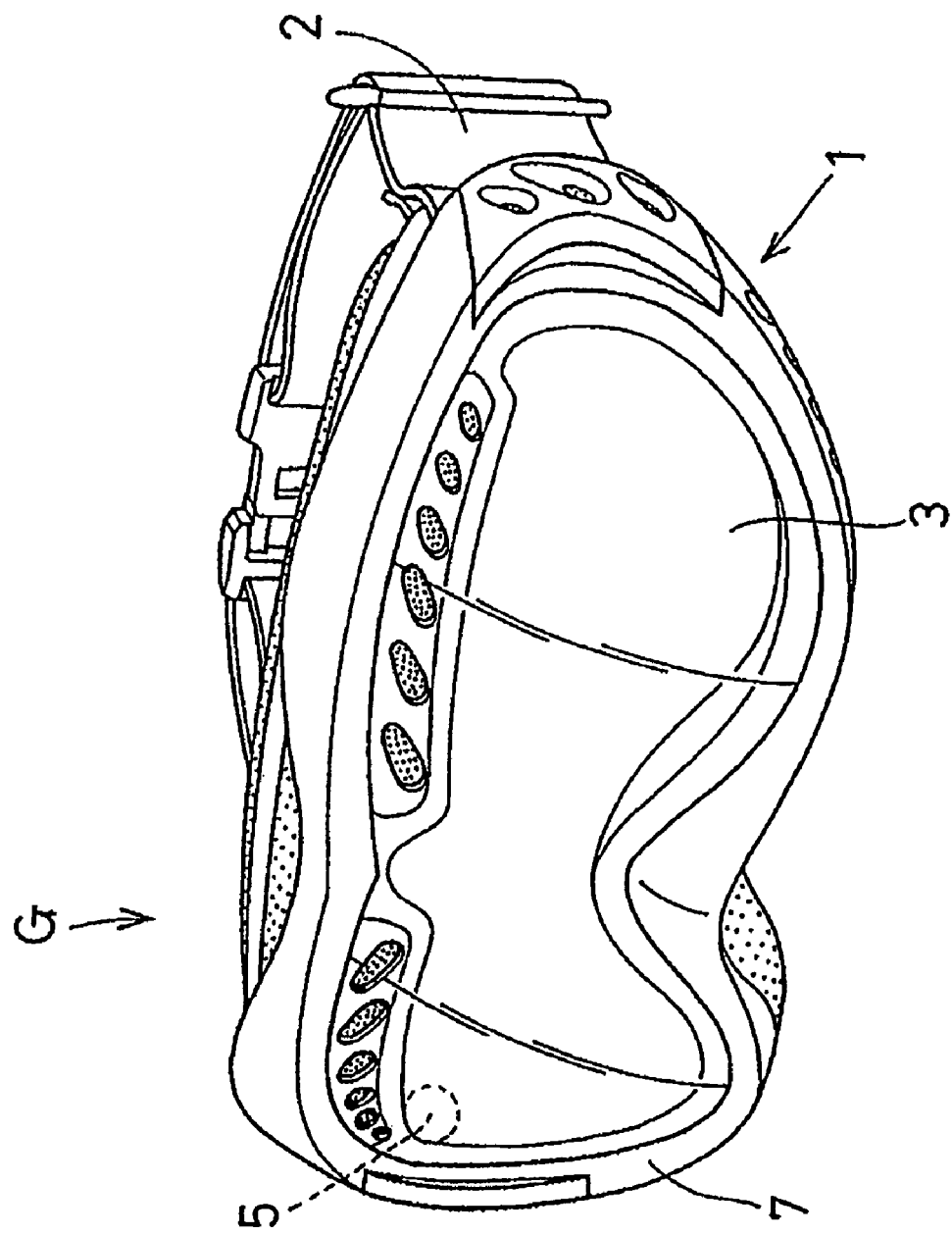
FIG. 1 is a perspective view of a protective device for eyes (goggles for skiing) of a first embodiment of the present invention.
Figure 2:
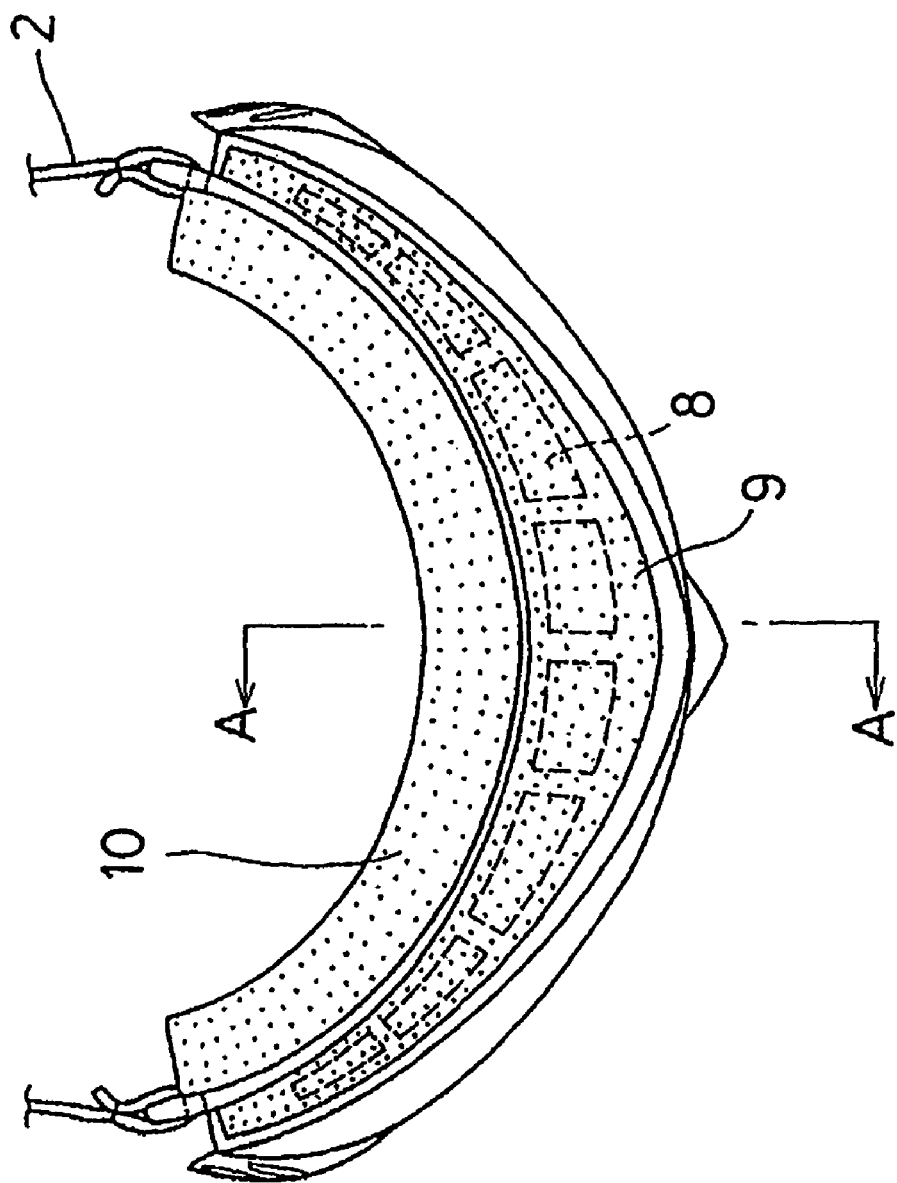
FIG. 2 is a top view of the goggles.
Figure 3:
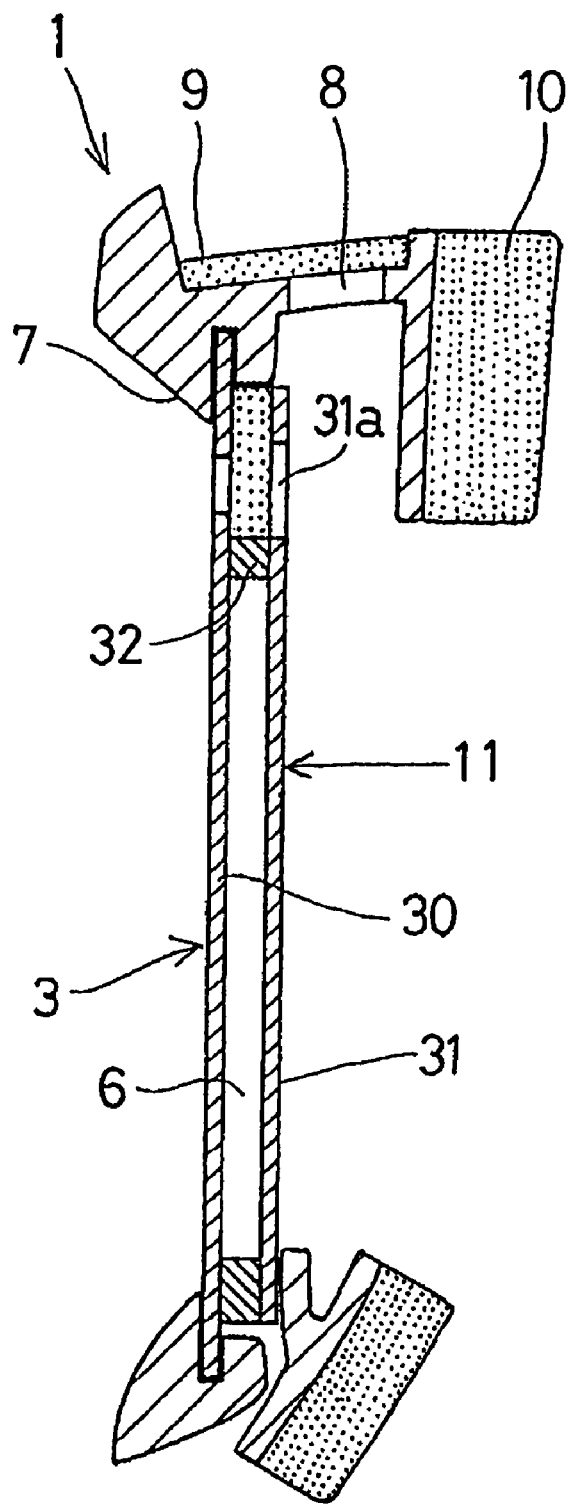
FIG. 3 is a cross-sectional view taken along the line A-A of FIG. 2.
Figure 4:
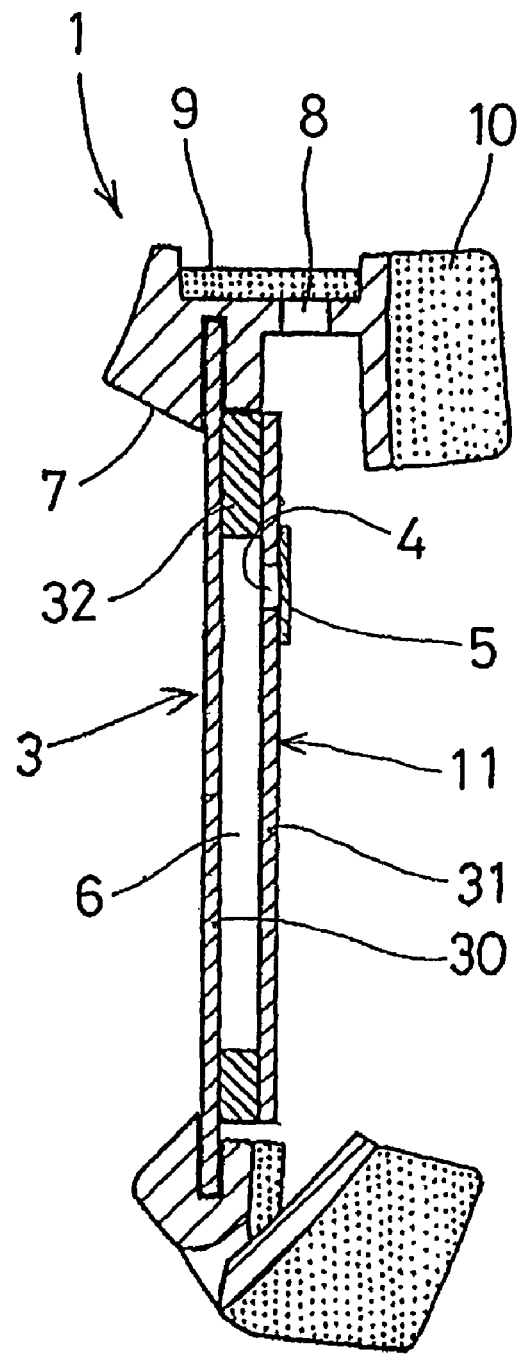
FIG. 4 is a cross-sectional view of the goggles cut vertically at a part where is pasted.
Figure 5:
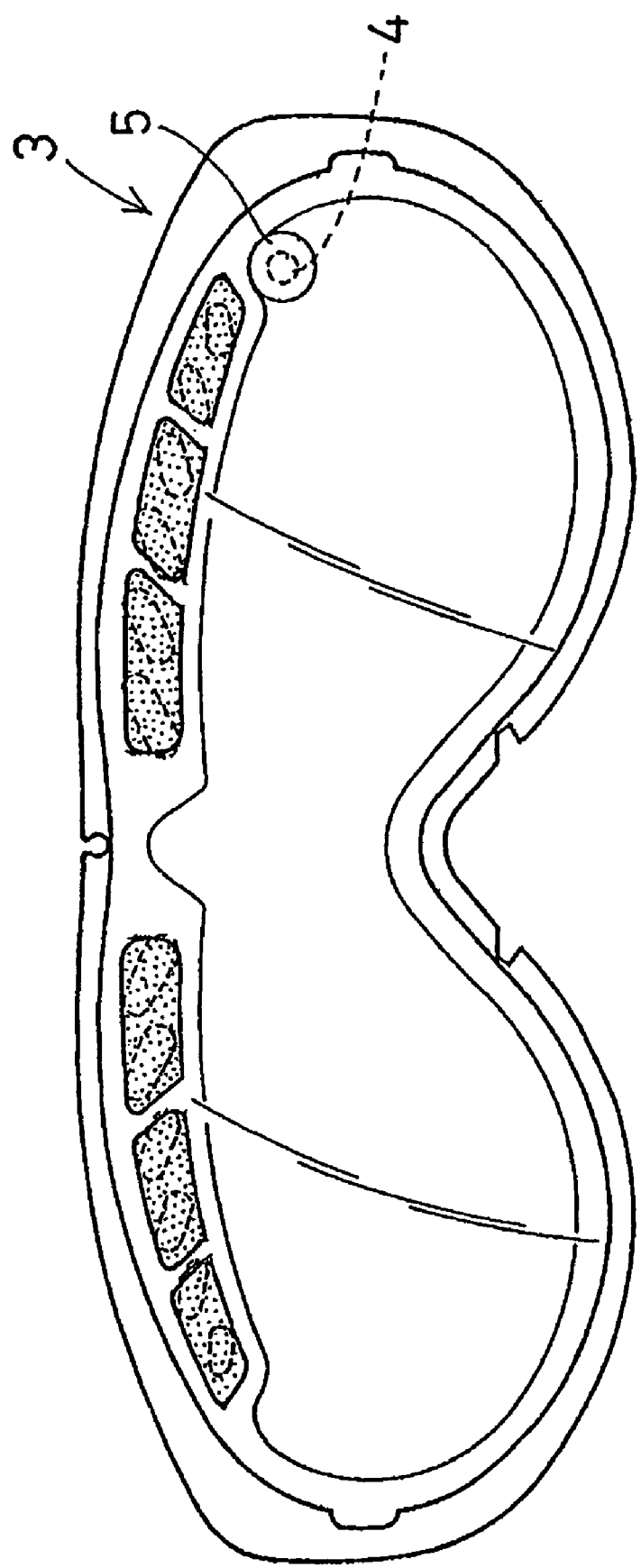
FIG. 5 is a view of the goggle lens used for the goggles viewed from the inner lens side.

FIG. 1 is a perspective view of a protective device for eyes (goggles for skiing) of a first embodiment of the present invention: FIG. 2 is a top view of the goggles: FIG. 3 is a cross-sectional view taken along the line A-A of FIG. 2: FIG. 4 is a cross-sectional view of the goggle cut vertically at a part where is pasted: and FIG. 5 is a view of the goggle lens used for the goggles viewed from the inner lens side.

As shown in FIG. 1 and FIG. 2, the goggles G for skiing includes a frame member 1, a belt member 2 joined to the frame member 1, a goggle lens 3 (a double lens member) attached to the frame member 1 in a freely detachable manner, a pressure adjusting mechanism 4 attached to the goggle lens 3, and a sheet 5.

The double lens member 3, as shown in FIG. 3, includes a front lens 30, a back lens 31 and a gasket 32. The front lens 30 and the back lens 31 made of a polycarbonate resin, a polyurethane resin, a polyester resin, or a polyamide resin are disposed approximately in parallel and fixed each other by a gasket 32, thereby making a space 6 surrounded with the front lens 30, the back lens 31 and the gasket 32.

The front lens 30 of the present invention is preferably made of one of a polycarbonate resin, a polyurethane resin, a polyester resin, and a polyamide resin in terms of the hardness, strength, and strong toughness.

The polycarbonate resin includes aromatic ring-containing aromatic polycarbonate resins having bisphenol A, alicyclic polycarbonate resins, and polymer alloys of polycarbonate resins and polyester resins.

Especially, aromatic ring-containing aromatic polycarbonate resins having bisphenol A and polymer alloys of the polycarbonate resins and polyester resins are preferable in terms of the hardness, strength, and strong toughness.

Among polyurethane resins containing aromatic isocyanates or alicyclic isocyanates as a main component of isocyanate components, the polyurethane resins which is not readily crystallized and has high transparency is preferable.

Among polyester resins containing aromatic dicarboxylic acids such as terephthalic acid as a main component of dicarboxylic acid components, the polyester resins having high transparency are preferable.

Polyamide resins having amorphous property and high transparency and containing alicyclic or aliphatic dicarboxylic acids and alicyclic or aliphatic diamines in molecules are preferable.

Among the above-mentioned polycarbonate resins, polyurethane resins, polyester resins and polyamide resins, polycarbonate resins are preferably used since they are excellent in the hardness of the resins, stiffness, and the strong toughness.

Especially, aromatic ring-containing aromatic polycarbonate resins having bisphenol A or polymer alloys of the polycarbonate resins and polyester resins, which have a viscosity average molecular weight of 15,000 or higher, preferably 18,000 or higher, of the polycarbonate resins are preferably recommended since they are excellent in strength and toughness and have high function of protecting a wearer putting on the protective device for eyes from impacts.

The front lens 30 is generally produced by an injection molding method, an extrusion molding method, or a method of polymerization between plates.

In the case of a polycarbonate resin, a polyurethane resin, a polyester resin, or a polyamide resin is formed into the front lens 30 by an injection molding method or a method of polymerization between plates, it is preferable to use a die having a cylindrical shape, an aspheric shape, or a spherical shape along a face of a wearer, so that the front glass 30 have the cylindrical shape, the aspheric shape or the spherical shape.

Especially, the aspheric shape or the spherical shape is preferable in terms of the stylish design and the readiness of the refractive correction.

Herein, the aspheric shape means a non-spherical shape, varying slightly from a perfectly spherical shape, and the aspheric shape is adopted for attractive appearances, or in order to avoid an optical distortion as much as possible in any part of the lens when the protective device for eyes is put on.

Further, the spherical shape means a perfect spherical shape and therefore a front curve and a back curve form a part of an arc in any transverse cross-sectional view of the lens.

Herein, the front curve means the curve of the lens facing to an object and the back curve means the curve of the lens facing to the eyes.

A lens designed to have an even thickness is called as a plano lens. Especially in the case of a transversely long plano lens just like that of goggles, since the impingent angle is getting to be acute towards the lens rim in the right and left and the path length in the lens becomes longer, the refractive power is generated and the distortions of vision tend to become significant. This is disadvantageous for a wearer of the goggles since the distortions of vision become more significant when he/she sees an object through the right or left end part of the lens.

In the case of an injection molding, the refractive power of the lens having an even thickness can be corrected by making the thickness of the lens thinner towards the lens rim.

That is, an aspheric die designed to make the lens thickness thinner from the center of the lens towards the lens rim on the basis of the optical theory for refraction correction is used to obtain an aspheric shape lens whose visual distortion has been corrected.

Similarly, a die having an adjusted back curve degree in relation to the front curve degree is used to make the thickness of the lens thinner towards the lens rim to obtain a spherical shape lens whose visual distortion has been corrected.

Herein, the curve degree means (1.523-1)/R in the case where the refractive index of the glass is 1.523 and the curvature radius is R (m).

With respect to the front lens 30 with no correction of the refractive power manufactured by an injection molding method, the lens thickness is in a range from 0.3 to 3 mm and preferably from 0.4 to 2.6 mm.

If the thickness is thinner than 0.3 mm, the physical strength of the lens becomes weak and if it exceeds 3 mm, the refractive power around the lens rim tends to become significant and therefore these are not preferable.

With respect to the front lens 30 with the corrected refractive power manufactured by an injection molding method, the lens center thickness is in a range from 0.8 to 4 mm and preferably from 1 to 3.6 mm.

If the center thickness is thinner than 0.8 mm, the physical strength in the lens rim tends to become weak and if it exceeds 4 mm, the lens tends to be heavy and therefore these are not preferable.

Further, the front lens 30 can be formed in a cylindrical shape using a cylindrical die. In the case of a cylindrical lens with no correction of the refractive power, the lens thickness is in a range from 0.3 to 3 mm and preferably 0.4 to 2.6 mm.

If the thickness is thinner than 0.3 mm, the physical strength of the lens becomes weak and if it exceeds 3 mm, the refractive power of the lens rim tends to become significant and therefore these are not preferable.

In the case of a cylindrical lens with a corrected refractive power, the lens center thickness is in a range from 0.8 to 4 mm and preferably 1 to 3.6 mm.

If the center thickness is thinner than 0.8 mm, the physical strength in the lens rim tends to become weak and if it exceeds 4 mm, the lens tends to be heavy and therefore these are not preferable.

Further, a resin sheet manufactured by an extrusion molding method, a method of polymerization between plates or the like can be used for the front lens 30. In this case, the above-mentioned polycarbonate resin, polyurethane resin, polyester resin, or polyamide resin may be extruded into a sheet-like shape through a slit or may be subjected to polymerization between plates or press-molded to produce a resin sheet with a thickness of 0.3 to 3 mm, preferably 0.4 to 2.6 mm and further formed into an aspheric, or spherical, or cylindrical shape.

If the sheet thickness is thinner than 0.3 mm, in the case where the sheet is used for goggles or shield lens, it likely to be bent or broken and if it exceeds 3 mm, the refractive power in the lens rim tends to become significant and therefore these are not preferable.

The method for forming into an aspheric, or spherical, or cylindrical shape is not particularly limited, however it is generally a method involving cutting the above-mentioned resin sheet into a proper size, setting the cut resin sheet in a die for forming, and thermally forming the resin sheet into a prescribed shape by hot air or a hot flatiron.

At the time of injection molding of the front lens 30, a polarizing plate or a photochromatic resin plate previously formed in the aspheric shape, the spherical shape or the cylindrical shape may be set in a die to carry out insert molding of the polarizing plate or the photochromatic resin plate in the front curve side.

Further, the surface of the front lens 30 may be hard-coated, subjected to an antireflection finish or water repellent finish to give the goggles an extra value.

Further, an extremely thin coating with a metallic or half-mirror-like property or specialized hues can be provided by a vacuum deposition technique or the like.

Further, for coloring, a dye or a pigment may be previously added to a substrate such as a polycarbonate resin, a polyurethane resin, a polyester resin, and a polyamide resin or they may be added after being formed into a lens or a resin sheet.

The same polycarbonate resin, polyurethane resin, polyester resin, or polyamide resin as that of the front lens 30 may be preferably used for the back lens 31 of the present invention in terms of the hardness, strength, and strong toughness of the resins.

The polycarbonate resin may include aromatic ring-containing aromatic polycarbonate resins having bisphenol A, alicyclic polycarbonate resins, and polymer alloys of polycarbonate resins and polyester resins.

Especially, aromatic ring-containing aromatic polycarbonate resins having bisphenol A, and polymer alloys of the polycarbonate resins and polyester resins are preferable in terms of the hardness, strength, and the strong toughness of the resins.

Among polyurethane resins containing aromatic isocyanates or alicyclic isocyanates as a main component of isocyanate components, the polyurethane resins which are not readily crystallized and has high transparency are preferably used.

Among polyester resins containing aromatic dicarboxylic acids such as terephthalic acid as a main component of dicarboxylic acid components, the polyester resins with high transparency are preferably used.

The polyamide resins having amorphous property and high transparency containing alicyclic or aliphatic dicarboxylic acids and alicyclic or aliphatic diamines in molecules are preferably used.

Among the above-mentioned polycarbonate resins, polyurethane resins, polyester resins and polyamide resins, polycarbonate resins are preferably used since they are excellent in the hardness of the resins, stiffness, and the strong toughness.

Especially, aromatic ring-containing aromatic polycarbonate resins having bisphenol A or polymer alloys of the polycarbonate resins and polyester resins, which have a viscosity average molecular weight of 15,000 or higher, preferably 18,000 or higher, of the polycarbonate resins are preferably recommended since they are excellent in strength and toughness and have high function of protecting a wearer putting on the protective device for eyes from impacts.

Similarly to the front lens 30, the back lens 31 of the invention can be produced by an injection molding method using a die or a method of polymerization between plates. In this case, not only a lens with an even thickness but also a lens with corrected refractive power can be produced.

Further, the lens with an even thickness can be produced from a resin sheet produced by an extrusion molding method, a method of polymerization between plates, a press molding method and the like.

Especially, in terms of the production easiness and the cost, a back lens produced from a resin sheet produced by an extrusion molding method, a method of polymerization between plates, or a press molding method is recommended.

The back lens 31 is preferable to have a thickness of 0.3 to 3 mm, preferably 0.4 to 2.6 mm.

If the lens thickness is thinner than 0.3 mm, the water vapor emitted from the skin while wearing the protective device for eyes is likely to permeate through the back lens and be transmitted into the space 6 formed by the front lens 30, the back lens 31 and the gasket 32 and due to the transmitted water vapor, the inside of the front lens 30, more particularly, the back curve side of the front lens 30, is likely to be fogged. This fogging frequently happens especially in cold environments such as skiing areas.

Further, if the lens thickness exceeds 3 mm, similarly to the front lens 30, the distortions of vision in the lens rim due to the refractive power tends to be significant.

The back lens 31 of the present invention is preferable to have an aspheric shape, a spherical shape, or a cylindrical shape almost same to that of the front lens 30. Both the front and back lens can be disposed approximately in parallel by making the shape of the back lens 31 similar to that of the front lens 30 and thus the double lens can be made to have good appearance.

A method for making the back lens 31 in order to have almost the same shape as that of the front lens 30, that is a method for making the back lens 31 to have the aspheric shape, the spherical shape or the cylindrical shape, is not particularly limited, however, the method is generally a method of using a die with a similar shape to that of the die for the front lens 30 or a method involving cutting a resin sheet for a back lens into a proper size, setting the cut resin sheet in a die for forming, and thermally forming the resin sheet into a prescribed shape by hot air, a hot flatiron or the like.

Alternatively, there are also the following methods: a method involving forming a resin sheet for the front lens 30 and a resin sheet for the back lens 31 into a double lens member 3 which the resin sheets have not previously formed into a particular shape and setting the double lens member into a goggle frame 1 having a lens fitting hole curved in a cylindrical shape while bending the double lens member into the cylindrical shape or a method of bending both lenses into a cylindrical shape when they are bonded with the gasket 32.

In the back curve side of the back lens 31, since the water vapor emitted from the skin while the protective device for eyes is in use causes a dew condensation, it is desirable to form an antifogging coating (layering a resin sheet 11 having an antifogging function) in at least the back curve side of the back lens 31.

Alternatively, a wearer of the goggles can apply a commercialized antifogging agent to the back curve side of the back lens 31.

Further, the back lens 31 can be provided with a functional film such as a hard coating or an evaporation film similar to that for the front lens 30.

The double lens member 3 of the present invention can be produced by bonding or adhering the front lens 30 and the back lens 31 produced in the above-mentioned manner via the gasket in the manner where both lenses are disposed approximately in parallel.

A substrate resin of the gasket 32 may be preferably polyurethane resins, synthetic rubbers, or elastomers and especially preferably resins or porous resins deformable by being pushed with fingers of a human and having elasticity sufficient to spontaneously restore the former shape and 40% or higher rupture elongation.

Particularly, a porous gasket is recommended because the porous gasket is easy to adjust its elasticity and elongation to proper extents and the porous gasket is lightweight.

When using the porous gasket, it is preferable to use a closed-cell-type porous gasket since in this type, the moisture from the sweat, snow, rain and the like are less likely to permeate into the double lens.

It is desirable that the gasket 32 is colored by a pigment or dye in terms of the good appearance of goggles, and especially a hue of an achromatic color type such as black and white tends to be preferable.

The gasket 32 may be a string-like gasket obtained by forming the above-mentioned substrate resin into a string-like shape with an equivalent diameter of 1 to 8 mm and preferably 3 to 6 mm.

If the equivalent diameter of the string-like gasket is shorter than 1 mm, the distance between the front lens 30 and the back lens 31 is not enough and thus both lenses are undesirably touched with each other and adhesive power tends to be lowered. If it exceeds 8 mm, it may possibly result in inferior appearance of the goggles.

In the case where the string-like gasket is used, there is a method for producing the double lens member 3 by putting the string-like gasket coated with a binding or adhesive agent between the peripheral parts of the back curve side of the front lens 30 and the front curve side of the back lens 31; layering and arranging the front lens 30 and the back lens 31 approximately in parallel; and if necessary, sticking and fixing both lenses by applying heat or pressure.

Further, as the gasket 32, a sheet-like gasket may be used. In this case, it is common to employ a method involving punching or cutting a sheet made of the above-mentioned substrate resin with a thickness of 0.5 to 7 mm, preferably 1 to 5 mm into an adhesive shape with a width of about 2 to 10 mm, preferably about 3 to 8 mm corresponding to the adhesion shape of the double lens 3 and sticking the front lens 30 and the back lens 31 with a binding or adhesive agent.

If the thickness of the gasket 32 is thinner than 0.5 mm, the distance between the front lens 30 and the back lens 31 is insufficient and thus both lenses tend to have contact with each other. If the thickness exceeds 7 mm, the appearance of the goggles tends to become inferior.

If the width of the gasket 32 is narrower than 2 mm, the adhesive strength of the binding or adhesive agent tends to become insufficient and if it exceeds 10 mm, the appearance of the goggles tends to become inferior.

Additionally, the width of the gasket 32 does not necessarily have to be always same but may be properly changed in consideration of the design property and the structural requirement. This is why it is said "about" 2 to 10 mm when describing the width of the gasket 32.

The most preferable gasket 32 of the invention is a sheet-like gasket in terms of easiness for production and workability. A method involving producing a circular or almost circular gasket 32 by punching or cutting a gasket sheet, which is obtained by applying a binding agent or an adhesive agent to both faces of a sheet and covering the sheet with a paper liner, corresponding to the adhesion shape of the double lens, peeling the paper liner, putting the gasket 32 in the back curve side of the front lens 30 or in the front curve side of the back lens 31, aligning the front lens 30 and the back lens 31 to make both lenses approximately in parallel, and sticking and fixing both lenses by applying heat or pressure, if necessary, to produce the double lens member 3 is most preferable in terms of the workability and reliability of the adhesion.

As the binding agent for the gasket 32, there are acrylic type and synthetic rubber type ones and as the adhesive agent, there are vinyl acetate type, cyanoacrylate type, polyurethane type, and elastomer type ones. In terms of the workability and the reliability of the adhesion, the binding agent is more preferable.

In the above-mentioned manner, one double lens member 3 including the front lens 30, the back lens 31, and the gasket 32 and having a space 6 surrounded with the front lens 30, the back lens 31, and the gasket 32 can be produced.

If rain or sweat penetrates this space 6 during sports or works, it causes fogging in the inside of the double lens member 3 and therefore it is preferable to use an unbroken annular gasket as the gasket 32 so that the space 6 becomes an air-tightly closed space. An unbroken annular gasket is also preferable in terms of the good appearance of the goggles.

However, in the case of a sport such as skiing and snowboarding which is accompanied with elevation changes many times a day by taking ski lifts or gondola lifts, if the space 6 is air-tightly closed, the double lens member 3 becomes expanded or compressed due to the atmospheric pressure fluctuation. As a result, almost all the atmospheric pressure fluctuating load is converged on the adhesion surface of the gasket where the lenses is thick and causing a separation of the gasket from the adhesion surface.

To prevent such disadvantage, the double lens member 3 of the present invention may be provided with a pressure adjusting mechanism 4 in the space 6 surrounded with the front lens 30, the back lens 31 and the gasket 32.

The pressure adjusting mechanism 4 may be provided either in the lenses or in the gasket 32.

In the case of being provided in the lenses, pin holes, pores, or slits as the pressure adjusting mechanism 4 are formed in lenses. Especially, it is recommended to provide them in the back lens 31 so as to obtain a better appearance in use.

In this case, at least one pressure adjusting hole is formed in the back lens 31. Especially, in terms of the good appearance, it is desired to form one pressure adjusting hole.

The shape of the pressure adjusting hole is not particularly limited, however it is preferable to make it circular or elliptical in order to maintain the physical strength of the lenses and also in terms of the good appearance.

Further, the pressure adjusting hole is recommended to have an equivalent diameter of 0.5 to 3 mm, preferably 0.6 to 2.5 mm. If the equivalent diameter is smaller than 0.5 mm, in the case where one pressure adjusting hole is formed, the pressure adjusting function tends to be insufficient and if it exceeds 3 mm, the appearance of goggles tends to become inferior.

It is preferable that the pressure adjusting hole is subjected to any waterproofing treatment. As the waterproofing method, it is recommended to employ a method of sticking a sheet 5 over the hole, which the sheet 5 has a water vapor permeability but impermeable to water.

As such the sheet 5 to be used, there are fluoro type finely porous sheets such as GORETEX (trade mark), polyurethane type sheets, interconnected-cell-type porous sheets with or without being subjected to a water-repelling agent treatment, waterproof fabrics sprayed or coated with a water-repelling agent, and fiber products obtained by weaving or knitting fibers subjected to water-repelling treatment.

These sheet-like materials may be stuck over the pressure adjusting hole of the lens by a biding agent or an adhesive agent.

In the case where the pressure adjusting mechanism 4 is provided in the gasket 32, at least one pressure adjusting hole is formed in the gasket 32.

As the pressure adjusting hole, it is recommended to form a small cut in the gasket 32. In the case of a porous gasket, an interconnected-cell-type porous gasket may be used.

In the case of forming a small cut in the gasket 32, in order to prevent penetration of rain and sweat from the outside, it is preferable to stick the above-mentioned sheet 5 has a water vapor permeability but impermeable to water, and in the case of using the porous gasket, it is preferable to be sprayed or applied with a water-repelling agent for waterproof.

The frame member 1, in the case of goggles, is a resin product including a goggle frame 1 having holes to fit the double lens 3 in and ventilation holes to the outside and a face attachment member.

A resin to be used for the goggle frame 1 is recommended to a resin having proper softness in terms of fitting workability of the double lens member 3 and face-fitting comfortableness.

The goggle frame 1 is generally an injection-molded structure body having a proper size for fitting the double lens member (30 and 31), a fitting rim 7 of the double lens 3 having a groove for fixation in the peripheral part, and ventilation holes 8 to the outside.

The double lens member 3 is fitted in the fitting rim 7 of the goggle frame 1 and fixed in the groove formed in the fitting rim 7. In some cases, it is possible to use a binding agent or an adhesive agent.

The ventilation holes 8 formed in the goggle frame 1 has a function of ventilating air to the outside for preventing the moisture, which is emitted from the skin, from being blocked inside the goggles in use. That is, the holes have a function of preventing the back curve side of the back lens 31 from being fogged caused by the moisture permeated into the double lens member 3 through the back lens 31.

The ventilation holes 8 of the goggle frame 1 are generally provided in the upper side, lateral side, or lower side of the goggle frame.

The size and the number of the holes are not particularly limited, however to improve the air permeability, it is preferable to be 1 $cm^2$ or wider.

Further, if the ventilation hole 8 is an opened hole, it is highly probable that rain, snow, or sweat enters into through the hole, and therefore, the ventilation hole 8 is generally preferable to be treated for waterproof. As the waterproofing method, it is recommended to stick a sheet 9 over the hole, which the sheet 9 has a water vapor permeability but impermeable to water.

As such a sheet 9, there are fluoro type finely porous sheets such as GORETEX (trade mark); polyurethane type sheets; interconnected-cell-type porous sheets, porous materials, or meshes with or without being subjected to a water-repelling agent treatment; waterproof fabrics sprayed or coated with a water-repelling agent; and fiber products obtained by weaving or knitting fibers subjected to water-repelling treatment.

These sheet-like materials, porous materials, or meshes may be stuck over the ventilation hole 8 of the goggle frame 1 with a binding agent or an adhesive agent.

Further, to improve the face-fitting property of the goggles, the goggle frame 1 is generally designed to be approximately cylindrical in accordance with the face structure.

In addition, the goggle frame member is generally provided with a face attachment body 10 in the portion where the goggle frame 1 and the face of a wearer are brought into contact with each other to improve the fitting property to the face and give no unpleasant feeling such as the pain or the itch to the face.

The face attachment body 10 is a kind of cushion materials made of a resin softer than the goggle frame 1. Due to the good feeling, porous resins are preferable. Either interconnected-cell-type or closed-cell-type resins may be used, however air-permeable interconnected-cell-type resins are preferable.

The goggle frame 1 and the face attachment body 10 are generally made of mutually different resins and both may be stuck to each other with a binding agent or an adhesive agent or fixed with a Velcro fastening.

Further, the frame member 1 of the invention for a shield, which is a shield frame, is designed that the double lens member 3 can be fitted or fixed with and the shield frame is usually provided with the face attachment body.

To the frame member 1 of the present invention, a belt member 2 for fixing the goggles on the face is attached. The belt member 2 is generally an elastic belt made of rubber or spandex and the belt member 2 may be provided with a length adjusting mechanism if necessary.

In the case of the shield frame of the present invention, a belt or an attachment for fixing it on the face or a helmet is provided to the shield frame.

A protective device for eyes such as goggles, face shielded helmets or shields according to the present invention is excellent in a function of protecting eyes from impacts, rain, snow, dust, or the like and excellent in the antifogging property in the double lens even in the case of sweating or ambient temperature fluctuation, as well as with high durability. These goggles, face shielded helmets or shields are preferably usable for sports such as skiing, snowboarding, ice skating, cycling, motocross motorcycling as well as industrial work sites for construction and civil engineering work.

Example 1

Preparation of Goggle (1) Preparation of front lens: A bisphenol A type polycarbonate resin sheet with a viscosity average molecular weight of about 22,000 and thickness of 1 mm was punched into a size of a front lens.

The front curve side of the front lens was mirrored by a vacuum deposition technique.

(2) Preparation of back lens: A bisphenol A type polycarbonate resin sheet with a viscosity average molecular weight of about 22,000 and thickness of 0.8 mm was punched into a size of a back lens.

(3) Preparation of gasket: A closed-cell type porous sheet made of 3 mm-thick chloroprene was coated with a binding agent in both surfaces and covered with further a paper liner and the resulting sheet was punched into the corresponding shape of the double lens so as to be a ring-shaped gasket with width of 5 mm.

(4) Preparation of double lens: The back lens was set in a cylindrical die almost same as the shape of a double lens fitting hole of a goggle frame. The paper liner in one side of the above-mentioned ring-shaped gasket was peeled off and the gasket was stuck to the back lens set in the die. Then, the paper liner in the other side was peeled off and the front lens was put theron facing to the back lens. The resulting unit was pushed to stick both lenses and obtain a double lens member having a cylindrical shape approximately same as the double lens fitting hole of the goggle frame and having an air-tightly closed space.

(5) Preparation of goggle frame: A goggle frame was prepared by injection molding of a polyurethane resin using a die designed in a cylindrical shape, having at least one hole for fitting the double lens member and four air permeation holes each having 1 $cm^2$ in size at the upper side of the goggle frame, and formed in accordance with the face structure of a wearer for easy fitness to the face.

(6) Waterproofing of air permeable hole of goggle frame: A 2 mm-thick interconnected-cell-type polyurethane sheet was stuck over the respective air permeation holes with a binding agent for waterproof.

(7) Installation of face attachment member to goggle frame: A 15 mm-thick interconnected-cell-type polyurethane sheet was cut into a shape of the face-contacting part of the goggle frame with 15 mm width to produce a ring-like face attachment member and the cut sheet was stuck to the goggle frame with a binding agent to produce the goggle frame member.

(8) Installation of double lens member to goggle frame member: The double lens member was set in the hole for fitting the double lens member of the goggle frame and fitted in the groove of the circumference of the fitting hole to fix the double lens member.

(9) Preparation of belt member for fixation-on-face: A belt member for fixation-on-face including a belt made of an elastic yarn produced by winding a synthetic fiber around rubber string and a clamp was fixed to the goggle frame member to produce the goggles.

(Antifogging Test)

The back curve side of the back lens of the above-mentioned goggles was coated with a commercialized antifogging solution. After putting on the goggle on the face at room temperature, the wearer moved into an environmental testing room at a temperature of −5° C. Even after one hour, fog was not generated inside of the double lens member.

(Peeling Strength Test of the Double Lens Member)

The above-mentioned goggles were repeatedly subjected to a depressurization test from 1 atmosphere to 0.95 atmosphere in a temperature of −5° C. Even after 500 times of repetition, the lenses were never peeled off the gasket.

Example 2

Preparation of Goggle (1) Preparation of front lens: A front lens with a front curve of 6 base lens curve, a back curve of 6.1 base lens curve, and a center thickness of 1.8 mm was produced by injection molding of a bisphenol A type polycarbonate resin sheet with a viscosity average molecular weight of about 22,000.

The front curve side of the front lens was mirrored by a vacuum deposition technique.

(2) Preparation of back lens and pressure adjusting hole: A 0.8 mm-thick resin sheet made of a bisphenol A type polycarbonate resin with a viscosity average molecular weight of about 20,000 was punched into a size approximately close to that of a front lens.

A circular hole with a diameter of 1 mm was punched to make a pressure adjusting hole at the position of the back lens corresponding to the space surrounded with the front lens, a back lens, and a gasket when assembled and as near as possible to the gasket.

Successively, the above-mentioned resin sheet was set in a die and thermally formed into a shape close to the back curve of the front lens to obtain a back lens.

(3) Preparation of gasket: A closed-cell-type sheet made of 3 mm-thick chloroprene coated with a bonding agent in both faces and covered with further paper liners was punched into a shape corresponding to the double lens and thereby producing a ring-like gasket with width of 5 mm.

(4) Preparation of double lens: The above-mentioned ring-like gasket was stuck to the back lens by peeling off the paper liner in one side of the gasket. Then, after peeling off the paper liner in the other side of the gasket, the front lens was set to the gasket so as to be in parallel to the back lens and both lenses were pushed to be stuck each other via the gasket.

(5) Waterproofing of pressure adjusting hole: The pressure adjusting hole with a diameter of 1 mm formed in the back lens was covered by a fluoro type porous film with a 3 mm diameter with a binding agent for waterproof.

(6) Preparation of goggle frame: A goggle frame was prepared by injection molding of a polyurethane resin using a die designed in a cylindrical shape, having at least one hole for fitting the double lens member and four air permeation holes each having 1 $cm^2$ in size at the upper side of the goggle frame, and formed in accordance with the face structure of a wearer for easy fitness to the face.

(7) Waterproofing of air permeable hole of goggle frame: A 2 mm-thick interconnected-cell-type polyurethane sheet was stuck over the respective air permeation holes with a binding agent for waterproof.

(8) Installation of face attachment member to goggle frame: A 15 mm-thick interconnected-cell-type polyurethane sheet was cut into a shape of the face-contacting part of the goggle frame with 15 mm width to produce a ring-like face attachment member and the cut sheet was stuck to the goggle frame with a binding agent to produce the goggle frame member.

(9) Installation of double lens member to goggle frame member: The double lens member was set in the hole for fitting the double lens member of the goggle frame and fitted in the groove of the circumference of the fitting hole to fix the double lens member.

(10) Preparation of belt member for fixation-on-face: A belt member for fixation-on-face including a belt made of an elastic yarn produced by winding a synthetic fiber around rubber string and a clamp was fixed to the goggle frame member to produce the goggles.

(Antifogging Test)

The back curve side of the back lens of the above-mentioned goggles was coated with a commercialized antifogging solution. After putting on the goggle on the face at room temperature, the wearer moved into an environmental testing room at a temperature of −5° C. Even after one hour, fog was not generated inside of the double lens member.

(Peeling Strength Test of the Double Lens Member)

The above-mentioned goggles were repeatedly subjected to a depressurization test from 1 atmosphere to 0.95 atmosphere in a temperature of −5° C. Even after 500 times of repetition, the lenses were never peeled off the gasket.

Example 3

Preparation of Goggle (1) Preparation of front lens: A front lens with a front curve of 6 base lens curve, a back curve of 6.1 base lens curve, and a center thickness of 1.8 mm was produced by injection molding of a transparent nylon resin ("Diamid" ZC 7500, manufactured by Daicel-Degussa, Ltd.).

The front curve side of the front lens was mirrored by a vacuum deposition technique.

(2) Preparation of back lens and pressure adjusting hole: A 1 mm-thick resin sheet made of the transparent nylon resin ("Diamid" ZC 7500, manufactured by Daicel-Degussa, Ltd.) was punched into a size approximately close to that of a back lens.

A circular hole with a diameter of 1 mm was punched to make a pressure adjusting hole at the position of the back lens corresponding to the space surrounded with the front lens, a back lens, and a gasket when assembled and as near as possible to the gasket.

Successively, the above-mentioned resin sheet was set in a die and thermally formed into a shape close to the back curve of the front lens to obtain a back lens.

(3) Preparation of gasket: A closed-cell-type sheet made of 3 mm-thick chloroprene coated with a bonding agent in both faces and covered with further paper liners was punched into a shape corresponding to the double lens and thereby producing a ring-like gasket with width of 5 mm.

(4) Preparation of double lens: The above-mentioned ring-like gasket was stuck to the back lens by peeling off the paper liner in one side of the gasket. Then, after peeling off the paper liner in the other side of the gasket, the front lens was set to the gasket so as to be in parallel to the back lens and both lenses were pushed to be stuck each other via the gasket.

(5) Waterproofing of pressure adjusting hole: The pressure adjusting hole with a diameter of 1 mm formed in the back lens was covered by a fluoro type porous film with a 3 mm diameter with a binding agent for waterproof.

(6) Preparation of goggle frame: A goggle frame was prepared by injection molding of a polyurethane resin using a die designed in a cylindrical shape, having at least one hole for fitting the double lens member, two air permeation holes each having 2 $cm^2$ size at the upper side of the goggle frame and two air permeation holes each having 2 $cm^2$ size at the lower side of the goggle frame, and formed in accordance with the face structure of a wearer for easy fitness to the face.

(7) Waterproofing of air permeable hole of goggle frame: A 2 mm-thick interconnected-cell-type polyurethane sheet was stuck over the respective air permeation holes with a binding agent for waterproof.

(8) Installation of face attachment member to goggle frame: A 15 mm-thick interconnected-cell-type polyurethane sheet was cut into a shape of the face-contacting part of the goggle frame with 15 mm width to produce a ring-like face attachment member and the cut sheet was stuck to the goggle frame with a binding agent to produce the goggle frame member.

(9) Installation of double lens member to goggle frame member: The double lens member was set in the hole for fitting the double lens member of the goggle frame and fitted in the groove of the circumference of the fitting hole to fix the double lens member.

(10) Preparation of belt member for fixation-on-face: A belt member for fixation-on-face including a belt made of an elastic yarn produced by winding a synthetic fiber around rubber string and a clamp was fixed to the goggle frame member to produce the goggles.

(Antifogging Test)

The back curve side of the back lens of the above-mentioned goggles was coated with a commercialized antifogging solution. After putting on the goggle on the face at room temperature, the wearer moved into an environmental testing room at a temperature of −5° C. Even after one hour, fog was not generated inside of the double lens member.

(Peeling Strength Test of the Double Lens Member)

The above-mentioned goggles were repeatedly subjected to a depressurization test from 1 atmosphere to 0.95 atmosphere in a temperature of −5° C. Even after 500 times of repetition, the lenses were never peeled off the gasket.

Comparative Example 1

Goggles were prepared in the same manner as Example 1, except that a 0.8 mm-thick propyl cellulose sheet was used for the back lens in place of the 0.8 mm-thick polycarbonate resin sheet used in Example 1.

When the antifogging test at a temperature of −5° C. was carried out in the same manner as that in Example 1, fog was generated inside of the double lens member after 10 minutes.

Comparative Example 2

Goggles were prepared in the same manner as Example 1, except that a 0.25 mm-thick polycarbonate resin sheet was used for the back lens in place of the 0.8 mm-thick polycarbonate resin sheet used in Example 1.

When the antifogging test at a temperature of −5° C. was carried out in the same manner as that in Example 1, fog was generated inside of the double lens member after 20 minutes.

Comparative Example 3

Goggles were prepared in the same manner as Example 2, except that no pressure adjusting hole was formed at the back lens.

(Antifogging Test)

The back curve side of the back lens of the above-mentioned goggles was coated with a commercialized antifogging solution. After putting on the goggle on the face at room temperature, the wearer moved into an environmental testing room at a temperature of −5° C. Even after one hour, fog was not generated inside of the double lens member.

(Peeling Strength Test of Double Lens Member)

The above-mentioned goggles were repeatedly subjected to a depressurization test from 1 atmosphere to 0.95 atmosphere in a temperature of −5° C. At the 20 times of repetition, the lenses were peeled off the gasket.

What is claimed is:

1. A protective device for eyes comprising a double lens member, a frame member and a face fixation member, wherein
    the double lens member includes a front lens, a back lens and a gasket;
    the front lens and the back lens are made of any one of polycarbonate resins, polyurethane resins, polyester resins, and polyamide resins; and
    the front lens and the back lens are disposed in parallel with the gasket therebetween to form a space surrounded with the front lens, the back lens and the gasket; and wherein
    the gasket is made of a resin with a thickness of about 0.5 to 7 mm and a width of about 2 to 10 mm; and a back curve side of the front lens and a front curve side of the back lens are fixed via the gasket with a binding agent or adhesive agent.

2. The protective device for eyes according to claim 1, wherein the front lens has any one of an aspheric shape, a spherical shape and a cylindrical shape, and is made thinner from a center toward a lens rim for a refraction collection.

3. The protective device for eyes according to claim 2, wherein the back lens is made from any one of a lens sheet and a molded sheet with a thickness of 0.3 to 3 mm, and has any one of an aspheric shape, a spherical shape and a cylindrical shape approximately same as the front lens.

4. The protective device for eyes according to claim 1, wherein
    the front lens is made from any one of a lens sheet and a molded sheet with a thickness of 0.3 to 3 mm;
    a back lens is made from a lens sheet with a thickness of 0.3 to 3 mm; and
    the double lens member has a cylindrical shape.

5. The protective device for eyes according to claim 1, wherein a back curve side of the back lens is treated with an antifogging agent.

6. The protective device for eyes according to claim 1, wherein a resin sheet with antifogging properties having any one of an aspheric shape, a spherical shape and a cylindrical shape approximately same as the back lens is layered on a back curve side of the back lens.

7. The protective device for eyes according to claim 1, wherein at least one pressure adjusting hole is provided at the back lens for a pressure adjustment of the space surrounded with the front lens, the back lens and the gasket.

8. The protective device for eyes according to claim 1, wherein at least one pressure adjusting hole is provided at the gasket for a pressure adjustment of the space surrounded with the front lens, the back lens and the gasket.

9. The protective device for eyes according to claim 1, wherein an air-permeable gasket is used for a pressure adjustment of the space surrounded with the front lens, the back lens and the gasket.

10. The protective device for eyes according to claim 7, wherein the pressure adjusting hole is covered with a breathable member which is permeable to water vapor but impermeable to water.

11. The protective device for eyes according to claim 8, wherein the pressure adjusting hole is covered with a breathable member which is permeable to water vapor but impermeable to water.

12. The protective device for eyes according to claim 9, wherein the air-permeable gasket is covered with a breathable member which is permeable to water vapor but impermeable to water.

* * * * *